United States Patent
Slonin et al.

(10) Patent No.: US 11,918,688 B2
(45) Date of Patent: *Mar. 5, 2024

(54) TREATMENT OF HIP PAIN WITH SUSTAINED-RELEASE LIPOSOMAL ANESTHETIC COMPOSITIONS

(71) Applicant: Pacira Pharmaceuticals, Inc., Parsippany, NJ (US)

(72) Inventors: Jonathan H. Slonin, Palm City, FL (US); Roy Winston, Parsippany, NJ (US); Stan Dysart, Marietta, GA (US)

(73) Assignee: Pacira Pharmaceuticals, Inc., Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/572,248

(22) Filed: Jan. 10, 2022

(65) Prior Publication Data

US 2022/0218610 A1 Jul. 14, 2022

Related U.S. Application Data

(60) Provisional application No. 63/135,849, filed on Jan. 11, 2021.

(51) Int. Cl.
*A61K 9/127* (2006.01)
*A61B 17/34* (2006.01)
(Continued)

(52) U.S. Cl.
CPC ............ *A61K 9/1271* (2013.01); *A61K 9/107* (2013.01); *A61K 9/127* (2013.01); *A61K 9/1277* (2013.01);
(Continued)

(58) Field of Classification Search
CPC ...... A61K 9/1271; A61K 9/107; A61K 9/127; A61K 9/1277; A61K 31/445; A61K 31/451; A61K 45/06; A61K 47/02
See application file for complete search history.

(56) References Cited

U.S. PATENT DOCUMENTS 5,316,771 A * 5/1994 Barenholz ............ A61K 9/1278
264/4.1
5,817,074 A 10/1998 Racz
(Continued)

FOREIGN PATENT DOCUMENTS

CN 109745607 5/2019
RU 2307675 10/2007
(Continued)

OTHER PUBLICATIONS

Domb, B.G., et al BMC Musculoskeletal Disorders, vol. 15, 310, pp. 1-6, 2014.*
(Continued)

*Primary Examiner* — Gollamudi S Kishore
(74) *Attorney, Agent, or Firm* — Fish & Richardson P.C.

(57) ABSTRACT

In some embodiments provided herein is a method of treating hip pain in a subject, the method comprising administering into the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

26 Claims, 1 Drawing Sheet

(51) Int. Cl.
*A61K 9/107* (2006.01)
*A61K 31/445* (2006.01)
*A61K 31/451* (2006.01)
*A61K 45/06* (2006.01)
*A61K 47/02* (2006.01)
*A61P 23/02* (2006.01)

(52) U.S. Cl.
CPC .......... *A61K 31/445* (2013.01); *A61K 31/451* (2013.01); *A61K 45/06* (2013.01); *A61K 47/02* (2013.01); *A61B 2017/3413* (2013.01); *A61P 23/02* (2018.01)

(56) References Cited

U.S. PATENT DOCUMENTS

| | | | |
|---|---|---|---|
| 8,182,835 | B2 | 5/2012 | Kim et al. |
| 8,410,140 | B2 | 4/2013 | Brummett |
| 8,834,921 | B2 | 9/2014 | Kim et al. |
| 8,906,966 | B2 | 12/2014 | Sherwood et al. |
| 8,957,779 | B2 | 2/2015 | Wu et al. |
| 8,975,268 | B2 | 3/2015 | Berde et al. |
| 8,975,281 | B2 | 3/2015 | Berde et al. |
| 9,192,575 | B2 | 11/2015 | Kim et al. |
| 9,205,052 | B2 | 12/2015 | Kim et al. |
| 9,585,838 | B2 | 3/2017 | Hartounian et al. |
| 10,398,648 | B2 | 9/2019 | Schutt et al. |
| 11,033,495 | B1 | 1/2021 | Hall et al. |
| 11,179,336 | B1 | 11/2021 | Hall et al. |
| 11,278,494 | B1 | 3/2022 | Hall et al. |
| 11,304,904 | B1 | 4/2022 | Hall et al. |
| 11,311,486 | B1 | 4/2022 | Hall et al. |
| 11,357,727 | B1 | 6/2022 | Hall et al. |
| 11,426,348 | B2 | 8/2022 | Hall et al. |
| 11,452,691 | B1 | 9/2022 | Hall et al. |
| 11,759,459 | B2 | 9/2023 | Winston et al. |
| 2002/0039596 | A1 | 4/2002 | Hartounian et al. |
| 2003/0059462 | A1* | 3/2003 | Barenholz .............. A61Q 17/04 514/762 |
| 2003/0069318 | A1 | 4/2003 | Dang et al. |
| 2003/0170288 | A1 | 9/2003 | Carr et al. |
| 2006/0078606 | A1* | 4/2006 | Kim ..................... A61K 31/167 424/450 |
| 2007/0249681 | A1 | 10/2007 | Sudo et al. |
| 2009/0105693 | A1 | 4/2009 | Ben-David et al. |
| 2009/0202436 | A1 | 8/2009 | Hobot et al. |
| 2011/0250264 | A1 | 10/2011 | Schutt et al. |
| 2012/0179038 | A1 | 6/2012 | Meurer et al. |
| 2013/0177633 | A1 | 7/2013 | Schutt et al. |
| 2013/0177634 | A1 | 7/2013 | Schutt et al. |
| 2013/0177635 | A1 | 7/2013 | Schutt et al. |
| 2013/0177636 | A1 | 7/2013 | Schutt et al. |
| 2013/0177637 | A1 | 7/2013 | Schutt et al. |
| 2013/0177638 | A1 | 7/2013 | Schutt et al. |
| 2013/0183372 | A1 | 7/2013 | Schutt et al. |
| 2013/0183373 | A1 | 7/2013 | Schutt et al. |
| 2013/0183375 | A1 | 7/2013 | Schutt et al. |
| 2013/0189349 | A1 | 7/2013 | Kim et al. |
| 2013/0195965 | A1 | 8/2013 | Schutt et al. |
| 2013/0306759 | A1 | 11/2013 | Schutt et al. |
| 2013/0344132 | A1 | 12/2013 | Kim et al. |
| 2014/0296293 | A1 | 10/2014 | Andersen et al. |
| 2015/0250724 | A1 | 9/2015 | Yamashita et al. |
| 2016/0000705 | A1 | 1/2016 | McDonald et al. |
| 2016/0089335 | A1 | 3/2016 | Ohri et al. |
| 2016/0361260 | A1 | 12/2016 | Schutt et al. |
| 2016/0375140 | A1 | 12/2016 | Ottoboni et al. |
| 2017/0007549 | A1 | 1/2017 | Yum et al. |
| 2018/0092847 | A1 | 4/2018 | Schutt et al. |
| 2019/0231762 | A1 | 8/2019 | Verity |
| 2022/0015738 | A1 | 1/2022 | Harbi et al. |
| 2022/0096116 | A1 | 3/2022 | McFarland et al. |
| 2022/0273564 | A1 | 5/2022 | Slonin et al. |
| 2022/0218613 | A1 | 7/2022 | Slonin et al. |
| 2022/0387318 | A1 | 12/2022 | Winston |
| 2023/0038098 | A1 | 2/2023 | Winston et al. |
| 2023/0042662 | A1 | 2/2023 | Los et al. |
| 2023/0052319 | A1 | 2/2023 | Winston et al. |
| 2023/0080593 | A1 | 3/2023 | Winston et al. |
| 2023/0087140 | A1 | 3/2023 | Winston et al. |
| 2023/0130180 | A1 | 4/2023 | Los et al. |

FOREIGN PATENT DOCUMENTS

| | | |
|---|---|---|
| WO | 97/03652 * | 2/1997 |
| WO | WO 1999/013865 | 3/1999 |
| WO | WO 1999/044640 | 9/1999 |
| WO | WO 2016/174661 | 11/2016 |
| WO | WO 2018/226732 | 12/2018 |
| WO | WO 2018/237109 | 12/2018 |
| WO | WO 2021/141956 | 7/2021 |
| WO | WO 2021/141959 | 7/2021 |
| WO | WO 2021/141963 | 7/2021 |

OTHER PUBLICATIONS

[No Author Listed] [online], "Highlights of Prescribing Information—EXPAREL," accessdata.fda.gov, Apr. 2018, retrieved on Jun. 17, 2022, retrieved from URL <www.accessdata.fda.gov/drugsatfda_docs/label/2018/022496s91bl.pdf>, 28 pages.

[No Author Listed] [online], "Marcaine [package insert]," accessdata.fda.gov, Oct. 2011, retrieved on Jun. 21, 2022, retrieved from URL <https://www.accessdata.fda.gov/drugsatfda_docs/label/2012/018692s0151bl.pdf>, 30 pages.

[No Author Listed] [online], "Naropin [package insert]," accessdata.fda.gov, Nov. 2018, retrieved on Jun. 21, 2022, retrieved from URL <https://www.accessdata.fda.gov/drugsatfda_docs/label/2018/020533s0351bl.pdf>, 30 pages.

American Society of Anesthesiologists Task Force on Acute Pain Management, "Practice guidelines for acute pain management in the perioperative setting: an updated report by the American Society of Anesthesiologists Task Force on Acute Pain Management," Anesthesiology, Feb. 2012, 116(2):248-273.

American Society of Anesthesiologists, "ASA Physical Status Classification System," asahq.org, Dec. 13, 2020, retrieved from URL <https://www.asahq.org/standards-and-guidelines/asa-physical-status-classification-system>, 4 pages.

Bigeleisen et al., "Novel approaches in pain management in cardiac surgery," Curr Opin Anaesthesiol. Feb. 2015, 28(1):89-94.

Biotechnology Innovation Organization "Re: Docket No. FDA-2019-N-2514: Standards for Future Opioid Analgesic Approvals and Incentives for New Therapeutics to Treat Pain and Addiction," Nov. 18, 2019, 11 pages.

Chughtai et al., "Liposomal Bupivacaine Is Both Safe and Effective in Controlling Postoperative Pain After Spinal Surgery in Children: A Controlled Cohort Study," Clin Spine Surg., 2020, 33(10):E533-E538.

Cohen et al., "Incidence of adverse events attributable to bupivacaine liposome injectable suspension or plain bupivacaine for postoperative pain in pediatric surgical patients: A retrospective matched cohort analysis," Paediatr Anaesth., 2019, 29(2):169-174, 15 pages.

Day et al., "Extended Release Liposomal Bupivacaine Injection (Exparel) for Early Postoperative Pain Control Following Pharyngoplasty," J Craniofac Surg., Jul. 2018, 29(3):726-730, 4 pages.

Duzlu et al., "Release Pattern of Liposomal Bupivacaine in Artificial Cerebrospinal Fluid," Turk J Anaesth Reanim., 2016, 44:1-6.

Ecoffey, "Refresher course: Local anesthetic pharmacology in children," Regional Anesthesia and Pain Medicine, 2015, 40(5):e23-e25.

FDA.gov [online] "Methodologies for Determining Opioid Sparing in Acute Pain Models," available on or before Dec. 14, 2019, via Internet Archive: Wayback Machine URL <http://web.archive.org/web/20191214114348/https://www.fda.gov/media/121206/download>, 61 pages.

Gan, "Poorly controlled postoperative pain: prevalence, consequences, and prevention," J Pain Res. 2017, 10:2287-2298.

(56) References Cited

OTHER PUBLICATIONS

Gerbershagen et al., "Pain intensity on the first day after surgery: a prospective cohort study comparing 179 surgical procedures," Anesthesiology, Apr. 2013, 118(4):934-944.
Globalnewswire.com [online], "Pacira—Exparel Achieves Primary and Key Secondary Endpoints in Phase 4 Choice Study in Cesarean Section Patients," Jan. 7, 2020, retrieved on Apr. 11, 2022, retrieved from URL <https://www.globenewswire.com/news-release/2020/01/07/1967140/0/en/EXPAREL-Achieves-Primary-and-Key-Secondary-Endpoints-in-Phase-4-CHOICE-Study-in-Cesarean-Section-Patients.html>, 6 pages.
Gottschalk et al., "Quality of postoperative pain using an intraoperatively placed epidural catheter after major lumbar spinal surgery," Anesthesiology, Jul. 2004, 101(1):175-180.
Hadzic et al., "Liposome Bupivacaine Femoral Nerve Block for Postsurgical Analgesia after Total Knee Arthroplasty," Anesthesiology, Jun. 2016, 124(6):1372-1383.
Hu et al., "Pharmacokinetic profile of liposome bupivacaine injection following a single administration at the surgical site," Clin Drug Investig., 2013, 33(2):109-115.
International Preliminary Report on Patentability in International Appln. No. PCT/US2021/012266, dated Jul. 12, 2022, 14 pages.
International Preliminary Report on Patentability in International Appln. No. PCT/US2021/012269, dated Jul. 21, 2022, 23 pages.
International Preliminary Report on Patentability in International Appln. No. PCT/US2021/012275, dated Jul. 12, 2022, 13 pages.
International Search Report and Written Opinion in International Appln. No. PCT/US2022/020713, dated Jun. 14, 2022, 24 pages.
Joshi et al., "The Safety of Liposome Bupivacaine Following Various Routes of Administration in Animals," Journal of Pain Research, 2015, 8:781-789.
Li et al., "Acute postoperative opioid consumption trajectories and long-term outcomes in pediatric patients after spine surgery," J Pain Res., 2019, 12:1673-1684.
Malinovsky et al., "Neurotoxicological Assessment After Intracisternal Injection of Liposomal Bupivacaine in Rabbits," Anesth. Analg., 1997, 85:1331-1336.
Manna et al., "Probing the mechanism of bupivacaine drug release from multivesicular liposomes," J Control Release, Jan. 28, 2019, 294:279-287, 41 pages.
Mazoit et al., "Pharmacokinetics of bupivacaine following caudal anesthesia in infants," Anesthesiology, Mar. 1, 1988, 68(3):387-391.
Nedeljkovic et al., "Liposomal Bupivacaine Transversus Abdominis Plane Block for Pain After Cesarean Delivery: Results From a Multicenter, Randomized, Double-Blind, Controlled Trial," PowerPoint, Presented at Society for Obstetric Anesthesia and Perinatology 51st Annual Meeting, Phoenix, AZ, May 1-5, 2019, 17 pages.
Nedeljkovic et al., "Transversus Abdominis Plane Block With Liposomal Bupivacaine for Pain After Cesarean Delivery in a Multicenter, Randomized, Double-Blind, Controlled Trial," Anesth. Analg., Dec. 2020, 131(6):1830-1839.
Oda, "Pharmacokinetics and systemic toxicity of local anesthetics in children," Journal of anesthesia, Jun. 16, 2016, 30(4):547-550.
Rabbitts et al., "Presurgical psychosocial predictors of acute postsurgical pain and quality of life in children undergoing major surgery," J Pain., Mar. 2015, 16(3):226-234.
Rabbitts et al., "Trajectories of postsurgical pain in children: risk factors and impact of late pain recovery on long-term health outcomes after major surgery," Pain, Nov. 2015, 156(11):2383-2389.
Rice et al., "Pharmacokinetic Profile and Tolerability of Liposomal Bupivacaine Following a Repeated Dose via Local Subcutaneous Infiltration in Healthy Volunteers," Clin Drug Investig., 2017, 37(3):249-257.
Scott et al., "Acute Toxicity of Ropivacaine Compared with that of Bupivacaine," Anesthesia and Analgesia, Nov. 1, 1989, 69(5):563-569.
Shah et al., "Current Trends in Pediatric Spine Deformity Surgery: Multimodal Pain Management and Rapid Recovery," Global Spine J., 2020, 10(3):346-352.
Springer et al., "Systemic Safety of Liposomal Bupivacaine in Simultaneous Bilateral Total Knee Arthroplasty," J Arthroplasty., Jan. 2018, 33(1):97-101.
Surdam et al., "The Use of Exparel (Liposomal Bupivacaine) to Manage Postoperative Pain in Unilateral Total Knee Arthroplasty Patients," Journal of Arthroplasty, 2015, 30:325-329.
Tirotta et al., "Continuous incisional infusion of local anesthetic in pediatric patients following open heart surgery," Pediatr Anaesth., Jun. 2009, 19(6):571-576.
USFaD, "Pediatric Study Plans: Content of and Process for Submitting Initial Pediatric Study Plans and Amended Initial Pediatric Study Plans Guidance for Industry," US Food and Drug Administration, Jul. 2020, retrieved from URL <https://www.fda.gov/media/86340/download>, 26 pages.
Walker et al., "Complications in Pediatric Regional Anesthesia: An Analysis of More than 100,000 Blocks from the Pediatric Regional Anesthesia Network," Anesthesiology, Oct. 2018, 129(4):721-732.
www.sec.gov [online], "Pacira BioSciences Reports First Quarter 2019 Revenues of $91.3 Million," May 2019, retrieved on Sep. 30, 2022, retrieved from URL <https://www.sec.gov/Archives/edgar/data/1396814/000139681419000012/pcrx- 3312019x991.htm>, 12 pages.
Zel et al., "Neurological and Histological Outcomes After Subarachnoid Injection of a Liposomal Bupivacaine Suspension in Pigs: A Pilot Study," British Journal of Anaesthesia, Mar. 2019, 122(3):379-387.
Perets et al. "Intraoperative Infiltration of Liposomal Bupivacaine vs Bupivacaine Hydrochloride for Pain Management in Primary Total Hip Arthroplasty: A Prospective Randomized Trial," The Journal of Arthroplasty, 2018, 33:441-446.
U.S. Appl. No. 17/719,716, filed Apr. 13, 2022, Hall et al.
U.S. Appl. No. 17/720,166, filed Apr. 13, 2022, Hall et al.
U.S. Appl. No. 17/840,104, filed Jun. 14, 2022, Hall et al.
U.S. Appl. No. 18/046,416, filed Oct. 13, 2022, Garcia et al.
U.S. Appl. No. 18/325,924, filed May 30, 2023, Hall et al.
U.S. Appl. No. 18/325,927, filed May 30, 2023, Hall et al.
[No Author Listed] [online], "Adductor Canal Block," RAUKvideos, uploaded on Jan. 29, 2021, retrieved on May 25, 2023, retrieved from URL <https://www.youtube.com/watch?v=DZLjNHkbMtI>, 2 pages [Video Submission].
[No Author Listed] [online], "Adductor Canal Block: What Nerves Are We After?," Regional Anesthesiology and Acute Pain Medicine, uploaded on Oct. 2, 2020, retrieved from internet on May 25, 2023, retrieved from URL <https://www.youtube.com/watch?v=fE4U7JQa2f8>, 2 pages [Video Submission].
Acharya et al., "Pericapsular Nerve Group Block: An Excellent Option for Analgesia for Positional Pain in Hip Fractures," Case Reports in Anesthesiology, Mar. 12, 2020, 2020,(1830136): 1-3.
Ackmann et al., "Anatomy of the Infrapatellar Branch in Relation to Skin Incisions and as the Basis to Treat Neuropathic Pain by Percutaneous Cryodenervation," Pain Physician Journal, May/Jun. 2014, 17:E229-E348.
Bagaria et al., "The feasibility of direct adductor canal block (DACB) as a part of periarticular injection in total knee arthroplasty," Knee Surgery & Related Research, 2020, 32(48), 7 pages.
Chin et al., "Mechanisms of action of fascial plane blocks: a narrative review," Regional Anesthesia and Pain Medicine, 2021, 46:618-628.
Epstein et al., "Plasma Bupivacaine Concentrations Following Iioinguinal-Iliohypogastric Nerve Blockade in Children," Anesthesiology, Nov. 1, 1988, 69(5):773-776.
Fiol et al., "Is There A Role for Liposomal Bupivacaine as Part of a Multimodal Strategy Inclusive of Intrathecal Morphine for Post-Cesarean Analgesia? A Retrospective Chart Review Study," Anesth. Pain Res., 2020, 4(2):1-6.
Greenky et al., "Intraoperative Surgeon Administered Adductor Canal Blockade Is Not Inferior to Anesthesiologist Administered Adductor Canal Blockade: A Prospective Randomized Trial," The Journal of Arthroplasty, 2020, 35:1228-1232.
International Preliminary Report on Patentability in International Application No. PCT/US2022/020713, dated Sep. 28, 2023, 18 pages.
International Preliminary Report on Patentability in International Appln. No. PCT/US2022/011828, dated Jul. 20, 2023, 16 pages.

(56) References Cited

OTHER PUBLICATIONS

Li et al., "Ultrasound-guided single popliteal sciatic nerve block is an effective postoperative analgesia strategy for calcaneal fracture: a randomized clinical trial," BMC Musculoskeletal Disorders, Jan. 2021, 22(735):1-9.

Matthews et al., "Surgeon-placed peripheral nerve block and continuous non-opioid analgesia in total knee arthroplasty is accessible intraoperatively: A cadaveric study," Journal of ISAKOS, Mar. 2023, 6 pages.

Matthews, "Continuous Adductor Canal & Periarticular Nerve Block for Total Knee Arthroplasty, Matthews' Placement Guide," Surgical Solutions, 2021, 6 pages.

MayfieldClinic.com [online], "Epidural Steroid Injections (ESI)," Mayfield Brain & Spine, Jul. 2018, retrieved on May 9, 2023, retrieved from URL <https://d3djccaurgtij4.cloudfront.net/pe-esi.pdf>, 3 pages.

Medilogbiohealth.com [online], "Angles of Administration of Injection—ID, IM, SC, IV," Mar. 10, 2021, retrieved on Aug. 22, 2023, retrieved from URL <https://www.medilogbiohealth.com/2021/03/injection.html>, 8 pages.

Mont et al., "Can Joint Arthroplasty Surgeons Safely Administer Anesthesia?," The Journal of Arthroplasty, 2020, 35:1169.

Pepper et al., "Intraoperative Adductor Canal Block for Augmentation of Periarticular Injection in Total Knee Arthroplasty: A Cadaveric Study," The Journal of Arthroplasty, 2016, 31:2072-2076.

Peterson et al., "Surgeon-Performed High-Dose Bupivacaine Periarticular Injection with Intra-Articular Saphenous Nerve Block is Not Inferior to Adductor Canal Block in Total Knee Arthroplasty," The Journal of Arthroplasty, May 2020, 35:1233-1238.

Regional Anesthesiology and Acute Pain Medicine [online], "Adductor Canal Block: What Nerves Are We After?," uploaded on Oct. 2, 2020, retrieved from URL <https://www.youtube.com/watch?v=fE4U7JQa2f>, 9 pages.

Rongstad et al., "Popliteal Sciatic Nerve Block for Postoperative Analgesia," Foot & Ankle International, Jul. 1996, 17(7):378-382.

Runge et al., "The Spread of Ultrasound-Guided Injectate From the Adductor Canal to the Genicular Branch of the Posterior Obturator Nerve and the Popliteal," Regional Anesthesia and Acute Pain, Dec. 2017, 42(6):725-730.

Stow et al., "Plasma bupivacaine concentrations during caudal analgesia and ilioinguinal-iliohypogastric nerve block in children," Anaesthesia, Aug. 1998, 43(8):650-653.

Sveom et al., "Ultrasound-Guided Adductor Canal Block Versus Intraoperative Transarticular Saphenous Nerve Block: A Retrospective Analysis," The Journal of Arthroplasty, 2022, 37:S134-S138.

Tak et al., "Continuous adductor canal block is superior to adductor canal block alone or adductor canal block combined with IPACK block (interspace between the popliteal artery and the posterior capsule of knee) in postoperative analgesia and ambulation following continued from U): total knee arthroplasty: randomized control trial," Musculoskeletal Surg., Jun. 2022, 106:155-162.

Teachmeanatomy.info [online], "Anatomical Planes," Sep. 30, 2022, retrieved on Jun. 13, 2023, retrieved from URL <https://teachmeanatomy.info/the-basics/anatomical-terminology/planes/>, 2 pages.

Tong et al., "Liposomal bupivacaine and clinical outcomes," Best Practice & Research Clinical Anesthesiology, 2014, 28:15-27.

Tran et al., "Evaluation of the proximal adductor canal block injectate spread: a cadaveric study," Reg. Anesth. Pain. Med., 2020, 45:124-130.

Vij et al., Liposomal Bupivacaine Decreases Post-Operative Opioid Use after Anterior Cruciate Ligament Reconstruction: A Review of Level I Evidence, Orthopedic Reviews, Aug. 5, 2022, 14(3):37159, 8 pages.

Worrell et al., "The Mayo block: an efficacious block for hallux and first metatarsal surgery," AANA Journal, Apr. 1, 1996, 64(2):146-152, Abstract only.

Yee et al., "Quadriceps Weakness After Single-Short Adductor Canal Block," The Journal of Bone and Joint Surgery, 2021, 103(1):30-36.

[No Author Listed] [online], "Full Prescribing Information—Exparel," exparel.com, revised Mar. 2022, retrieved on Apr. 14, 2022, retrieved from URL <https://www.exparel.com/hcp/prescribing-information.pdf?msclkid=60c82e5b2c231a2fdbe94c034f355fb2&utm_source=bing&utm_medium=cpc&utm_campaign=HCP%20-%20Branded&utm_term=exparel%20dosing%20information&utm_content=Dosage>, 36 pages.

Laura Girón-Arango et al., "Pericapsular Nerve Group (PENG) Block for Hip Fracture", Reg Anesth Pain Med, 2018, 43:859-863, 5 pages.

International Search Report and Written Opinion in International Appln. No. PCT/US2022/011828, dated Apr. 1, 2022, 18 pages.

Patel et al., "Brachial Plexus Block with Liposomal Bupivacaine for Shoulder Surgery Improves Analgesia and Reduces Opioid Consumption: Results from a Multicenter, Randomized, Double-Blind, Controlled Trial," Pain Medicine, 2019, 21(2):387-400, 14 pages.

Ahiskalioglu et al., "Can high volume pericapsular nerve group (PENG) block act as a lumbar plexus block?" Journal of Clinical Anesthesia, May 2020, 61:109650, 2 pages.

Delgado et al., "Validation of Digital Visual Analog Scale Pain Scoring With a Traditional Paper-based Visual Analog Scale in Adults," J Am Acad Orthop Surg Glob Res Rev., Mar. 2018, 2(3):e088, 6 pages.

Ginosar et al., "ED50 and ED95 of Intrathecal Hyperbaric Bupivacaine Coadministered with Opioids for Cesarean Delivery," Anesthesiology, Mar. 2004, 100(3):676-682.

Giron Arango et al., "Reply to Dr Yu et al: Inadvertent quadriceps weakness following the pericapsular nerve group (PENG) block," Reg Anesth Pain Med, May 2019, 44(5):613-614.

International Search Report and Written Opinion in International Appln. No. PCT/US2021/012266, dated Apr. 30, 2021.

International Search Report and Written Opinion in International Appln. No. PCT/US2021/012269, dated Mar. 25, 2021, 25 pages.

International Search Report and Written Opinion in International Appln. No. PCT/US2021/012275, dated Mar. 25, 2021, 14 pages.

Kim et al., "Preparation of multivesicular liposomes," Biochim. Biophys. Acta—Biomembranes, Mar. 9, 1983, 728(3):339-348.

Malik et al., "Emerging roles of liposomal bupivacaine in anesthesia practice," Journal of Anaesthesiology Clinical Pharmacology, April0June 2017, 33(2):151-156.

Peng et al., "Reply to Dr Nielsen: Pericapsular Nerve Group (PENG) block for hip fracture," Reg Anesth Pain Med, Mar. 2019, 44(3):415-416.

Raja et al., "The revised International Association for the Study of Pain definition of pain: concepts, challenges, and compromises," PAIN, Sep. 1, 2020, 161(9):1976-1982.

Santos et al., "Is Continuous PENG Block the New 3-in-1?" J Anesth Clin Res 2019, Jun. 28, 2019, 10(6):1000898, 2 pages.

Short et al., "Anatomic Study of Innervation of the Anterior Hip Capsule: Implication for Image-Guided Intervention," Regional Anesthesia and Pain Medicine, Feb. 2018, 43(2):186-192.

Tran et al.., "Is pericapsular nerve group (PENG) block a true pericapsular block?," Reg Anesth Pain Med, Feb. 2019, 44(2):257.

Yu et al., "Inadvertent quadriceps weakness following the pericapsular nerve group (PENG) block," Reg Anesth Pain Med, May 2019, 44(5):611-613.

Beachler et al. "Liposomal bupivacaine in total hip arthroplasty: Do the results justify the cost?" Journal of Orthopaedics, 2017, 14:161-165.

Bronson et al. "Unanticipated transient sciatic nerve deficits from intra-wound liposomal bupivacaine injection during total hip arthroplasty," Arthroplasty Today, 2015, 1:21-24.

McGraw-Tatum et al. "A Prospective, Randomized Trial Comparing Liposomal Bupivacaine vs Fascia Iliaca Compartment Block for Postoperative Pain Control in Total Hip Arthroplasty," The Journal of Arthroplasty, 2017, 32:2181-2185.

de Leeuw et al., "The Psoas Compartment Block for Hip Surgery: The Past, Present, and Future," Anesthesiology Research and Practice, 2011, Article ID 159541, pp. 1-6.

Mannion et al., "In with the New, Out with the Old? Comparison of Two Approaches for Psoas Compartment Block," Anesthesia and Analgesia, 2005, 101:259-264.

(56) References Cited

OTHER PUBLICATIONS

Mannion, "Psoas Compartment Block," Continuing Education in Anesthesia, Critical Care & Pain, 2007, 7(5):162-166.
Therapy Services Patient Information [online] "Pubic Rami Fracture," retrieved on Jan. 11, 2023, retrieved from URL <https://www.uhd.nhs.uk/uploads/about/docs/our_publications/patient_information_leaflets/orthopaedics/Pubic_rami_fracture.pdf>, 12 pages.
U.S. Appl. No. 17/790,426, filed Jun. 30, 2022, Winston et al.
U.S. Appl. No. 17/958,780, filed Oct. 3, 2022, Winston et al.

\* cited by examiner

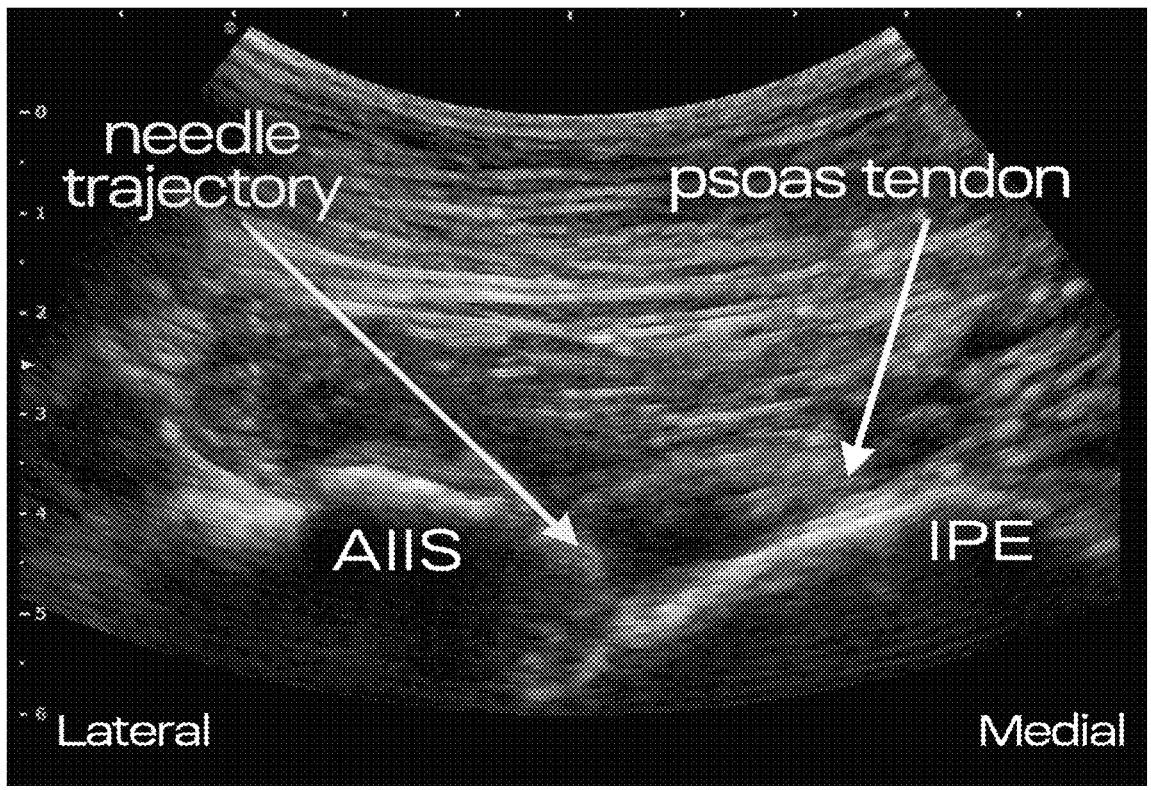

TREATMENT OF HIP PAIN WITH SUSTAINED-RELEASE LIPOSOMAL ANESTHETIC COMPOSITIONS

CROSS-REFERENCE TO RELATED APPLICATIONS

This application claims the benefit of U.S. Provisional Application No. 63/135,849, filed Jan. 11, 2021, which is incorporated by reference herein in its entirety.

BACKGROUND

Pain is described by the International Association for the Study of Pain as "an unpleasant sensory or emotional experience associated with actual or potential tissue damage, or described in terms of such damage." See Raja, Srinivasa N.a, et al., "The revised International Association for the Study of Pain definition of pain: concepts, challenges, and compromises," PAIN: September 2020—Volume 161—Issue 9—p 1976-1982, doi: 10.1097/j.pain.0000000000001939. As such the expression and perception of pain is a complex phenomenon and has multiple etiologies and factors that impact on the perception of pain. The perception of pain varies in duration, frequency and pattern depending on the origin and chronicity.

Hip and pelvic associated hip pain is a clinical manifestation of a pathological condition in and around the hip joint and involves both acute and chronic processes. Hip pain may be referred from other pathologic areas such as the spine or internal organs or may have an origin with pathology in and around the hip joint. Acute hip pain is often limited and resolves with the appropriate nonsurgical and surgical treatment while chronic pain is a long-term condition requiring ongoing treatment depending on the diagnosis. Hip pain as a general category includes the pain associated with disease processes and inflammatory conditions and also includes pain associated with injury or trauma, such as hip or pelvic fracture, dislocations and tears as well as overuse syndromes, structural abnormalities to include hip dysplasia and femoral acetabular impingement, hip degenerative conditions to include osteoarthritis and as well as the pain associated with surgery to include treatment of hip fracture and hip trauma, hip replacement surgery, along with pelvic osteotomy and pelvic reconstructive surgery.

Hip pain whether due to an inflammatory or ongoing disease process or structural abnormality results in reduced quality of life and in many cases significant functional disability. Pain associated in and around the hip joint is recognized as a leading cause of impairment of mobility. Continued or chronic pain results in significant emotional and psychological maladaptive responses and adaptive social responses include reduction in participation in activities and interaction with peers.

Thus, there continues to be a need for methods of treating hip pain in a subject.

SUMMARY

In some embodiments provided herein is a method of treating hip pain in a subject, the method comprising administering into the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine or a salt thereof, such as the hydrochloride salt, wherein the aqueous phase is encapsulated within the multivesicular liposome.

In some embodiments provided herein is a method of treating hip pain in a subject, the method comprising administering into the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of treating hip pain in a subject, the method comprising administering into the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of treating hip pain in a subject, the method comprising administering into the subject a pharmaceutical composition comprising multivesicular liposomes encapsulating bupivacaine phosphate, said multivesicular liposomes comprising:
   bupivacaine or a salt thereof;
   phosphoric acid;
   a lipid component comprising at least one amphipathic lipid and at least one neutral lipid lacking a hydrophilic head group; and,
   optionally, a cholesterol and/or a plant sterol wherein said multivesicular liposomes are made by a process comprising:
   a) preparing a first aqueous component comprising phosphoric acid;
   b) preparing a lipid component comprising at least one organic solvent, at least one amphipathic lipid, and at least one neutral lipid lacking a hydrophilic head group;
   c) mixing said first aqueous component and said lipid component to form a water-in-oil emulsion, wherein at least one component comprises bupivacaine or a salt thereof;
   d) mixing said water-in-oil emulsion with a second aqueous component to form solvent spherules; and
   e) removing the organic solvent from the solvent spherules to form multivesicular liposomes encapsulating bupivacaine phosphate.

In some embodiments provided herein is a method of treating hip pain in a subject, the method comprising administering into the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of treating hip pain in a subject, the method comprising administering into the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of treating hip pain in a subject, the method comprising administering into the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments, the method of treating hip pain in a subject comprises administering an opioid to the subject following completion of a treatment as disclosed herein.

In some embodiments, the opioid is administered in a total amount less than 50 mg in the first about 72 hours following completion of a treatment as disclosed herein.

In some embodiments of the method of treating hip pain in a subject, wherein the subject is a first subject, in the first about 72 hours following completion of the treatment the opioid is administered to the first subject in a total amount that is lower than the total amount of an opioid that is administered to a second subject in the first about 72 hours following completion of hip treatment in the second subject, wherein a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, is not administered to the second subject.

In some embodiments of the method of treating hip pain in a subject, wherein the subject is a first subject, in the first about 72 hours following completion of the treatment the opioid is administered to the first subject in a total amount that is lower than the total amount of an opioid that is administered to a second subject in the first about 72 hours following completion of treatment in the second subject, wherein a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome, is not administered to the second subject.

In some embodiments of the method of treating hip pain in a subject, wherein the subject is a first subject, in the first about 72 hours following completion of the treatment the opioid is administered to the first subject in a total amount that is lower than the total amount of an opioid that is administered to a second subject in the first about 72 hours following completion of treatment in the second subject, wherein a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate,
  is not administered to the second subject.

In some embodiments of the method of treating hip pain in a subject, wherein the subject is a first subject, in the first about 72 hours following completion of the treatment the opioid is administered to the first subject in a total amount that is lower than the total amount of an opioid that is administered to a second subject in the first about 72 hours following completion of treatment in the second subject, wherein a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, is not administered to the second subject.

In some embodiments of the method of treating hip pain in a subject, wherein the subject is a first subject, in the first about 72 hours following completion of the treatment the opioid is administered to the first subject in a total amount that is lower than the total amount of an opioid that is administered to a second subject in the first about 72 hours following completion of treatment in the second subject, wherein a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, is not administered to the second subject.

In some embodiments of the method of treating hip pain in a subject, wherein the subject is a first subject, in the first about 72 hours following completion of the treatment the opioid is administered to the first subject in a total amount that is lower than the total amount of an opioid that is administered to a second subject in the first about 72 hours following completion of treatment in the second subject, wherein a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles, is not administered to the second subject.

BRIEF DESCRIPTION OF THE DRAWINGS

FIG. 1 shows an example needle trajectory for administration of a pharmaceutical composition as disclosed herein.

DEFINITIONS

As used herein, "hip treatment" is a treatment of an injury, of a procedure, or of a disease process, in the hip or pelvic region. Examples of hip treatment include treatment of a hip fracture, treatment of hip trauma, hip surgery, hip replacement, hip arthroplasty, and pelvic osteotomy and pelvic reconstructive surgery.

As used herein, "hip pain" is any pain associated with an injury, procedure, or disease process, in the hip or pelvic region. Examples of hip pain include pain associated with disease processes and inflammatory conditions and pain associated with injury or trauma, such as hip or pelvic fracture, pain associated with dislocations and tears as well as over use syndromes, pain associated with structural abnormalities including hip dysplasia and femoral acetabular impingement, pain associated with hip degenerative conditions to include osteoarthritis, and pain associated with surgery including treatment of hip fracture and hip trauma, hip replacement surgery, and pelvic osteotomy and pelvic reconstructive surgery.

As used herein, "treatment of hip pain" or "hip pain treatment" is the treatment of any hip pain as defined herein.

DETAILED DESCRIPTION

In some embodiments provided herein is a method of treating hip pain in a subject, the method comprising administering into the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of treating hip pain in a subject, the method comprising administering into the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of treating hip pain in a subject, the method comprising administering into the subject a pharmaceutical composition comprising multivesicular liposomes encapsulating bupivacaine phosphate, said multivesicular liposomes comprising:
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.

In some embodiments provided herein is a method of treating hip pain in a subject, the method comprising administering into the subject a multivesicular liposomal particle pharmaceutical composition made by a process comprising:
a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of treating hip pain in a subject, the method comprising administering into the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of treating hip pain in a subject, the method comprising administering into the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of anesthetizing a subject in need of anesthetization prior to hip treatment, the method comprising administering into the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of anesthetizing a subject in need of anesthetization prior to hip treatment, the method comprising administering into the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of anesthetizing a subject in need of anesthetization prior to hip treatment, the method comprising administering into the subject a pharmaceutical composition comprising multivesicular liposomes encapsulating bupivacaine phosphate, said multivesicular liposomes comprising:
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.

In some embodiments provided herein is a method of anesthetizing a subject in need of anesthetization prior to hip treatment, the method comprising administering into the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of anesthetizing a subject in need of anesthetization prior to hip treatment, the method comprising administering into the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of anesthetizing a subject in need of anesthetization prior to hip treatment, the method comprising administering into the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of anesthetizing a subject in need of anesthetization during hip treatment, the method comprising administering into the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of anesthetizing a subject in need of anesthetization during hip treatment, the method comprising administering into the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of anesthetizing a subject in need of anesthetization during cesarean section surgery, the method comprising administering into the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate.

In some embodiments provided herein is a method of anesthetizing a subject in need of anesthetization during hip treatment, the method comprising administering into the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of anesthetizing a subject in need of anesthetization during hip treatment, the method comprising administering into the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one frit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of anesthetizing a subject in need of anesthetization during to hip treatment, the method comprising administering into the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of anesthetizing a subject in need of anesthetization following hip treatment, the method comprising administering into the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of anesthetizing a subject in need of anesthetization following cesarean section surgery, the method comprising administering into the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of anesthetizing a subject in need of anesthetization following cesarean section surgery, the method comprising administering into the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate.

In some embodiments provided herein is a method of anesthetizing a subject in need of anesthetization following hip treatment, the method comprising administering into the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of anesthetizing a subject in need of anesthetization following hip treatment, the method comprising administering into the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one frit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of anesthetizing a subject in need of anesthetization following hip treatment, the method comprising administering into the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of reducing hip pain in a subject, the method comprising administering into the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of reducing hip pain in a subject, the method comprising administering into the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of reducing hip pain in a subject, the method comprising administering into the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate.

In some embodiments provided herein is a method of reducing hip pain in a subject, the method comprising administering into the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of reducing hip pain in a subject, the method comprising administering into the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of reducing hip pain in a subject, the method comprising administering into the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of reducing an amount of opioid administered to a subject following hip treatment, the method comprising administering into the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of reducing an amount of opioid administered to a subject following hip treatment, the method comprising administering into the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of reducing a duration of time during which an opioid is administered to a subject following hip treatment, the method comprising administering into the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate.

In some embodiments provided herein is a method of reducing an amount of opioid administered to a subject following hip treatment, the method comprising administering into the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of reducing an amount of opioid administered to a subject following hip treatment, the method comprising administering into the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of reducing an amount of opioid administered to a subject following hip treatment, the method comprising administering into the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of reducing a duration of time during which an opioid is administered to a subject following hip treatment, the method comprising administering into the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of reducing a duration of time during which an opioid is administered to a subject following hip treatment, the method comprising administering into the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of reducing a duration of time during which an opioid is administered to a subject following hip treatment, the method comprising administering into the subject a pharmaceutical composition comprising multivesicular liposomes encapsulating bupivacaine phosphate, said multivesicular liposomes comprising:
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate.

In some embodiments provided herein is a method of reducing a duration of time during which an opioid is administered to a subject following hip treatment, the method comprising administering into the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of reducing a duration of time during which an opioid is administered to a subject following hip treatment, the method comprising administering into the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of reducing a duration of time during which an opioid is administered to a subject following hip treatment, the method comprising administering into the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of reducing an amount of a non-opioid analgesic administered to a subject following hip treatment, the method comprising administering into the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of reducing an amount of a non-opioid analgesic administered to a subject following hip treatment, the method comprising administering into the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of reducing an amount of a non-opioid analgesic administered to a subject following hip treatment, the method comprising administering into the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate.

In some embodiments provided herein is a method of reducing an amount of a non-opioid analgesic administered to a subject following hip treatment, the method comprising administering into the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of reducing an amount of a non-opioid analgesic administered to a subject following hip treatment, the method comprising administering into the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of reducing an amount of a non-opioid analgesic administered to a subject following hip treatment, the method comprising administering into the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
  wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

In some embodiments provided herein is a method of reducing a duration of time during which a non-opioid analgesic is administered to a subject following hip treatment, the method comprising administering into the subject a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments provided herein is a method of reducing a duration of time during which a non-opioid analgesic is administered to a subject following hip treatment, the method comprising administering into the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome.

In some embodiments provided herein is a method of reducing a duration of time during which a non-opioid analgesic is administered to a subject following hip treatment, the method comprising administering into the subject a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate.

In some embodiments provided herein is a method of reducing a duration of time during which a non-opioid analgesic is administered to a subject following hip treatment, the method comprising administering into the subject a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi.

In some embodiments provided herein is a method of reducing a duration of time during which a non-opioid analgesic is administered to a subject following hip treatment, the method comprising administering into the subject a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns.

In some embodiments provided herein is a method of reducing a duration of time during which a non-opioid analgesic is administered to a subject following hip treatment, the method comprising administering into the subject a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
  wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles.

Pharmaceutical compositions described herein are delivered to a target area within the subject. In various example embodiments, the pharmaceutical composition is administered by an image-guided (e.g., ultrasound) needle injection. For example, the pharmaceutical composition is administered by a needle injection using an in-plane mode of insertion relative to an ultrasound imaging transducer. Alternatively or additionally, the needle is advanced using an out-of-plane mode of insertion. In an example embodiment, the pharmaceutical composition is administered by needle injection using an in-plane mode of insertion. In an example embodiment, the pharmaceutical composition is administered by needle injection using an in-plane mode of insertion relative to an imaging transducer. An injection needle is advanced to one or more target locations within the subject where the pharmaceutical composition is dispensed. In an example embodiment, administering the composition includes advancing a needle tip of the injection needle from a subject access location proximate the inguinal crease along a cephalad-to-caudad and lateral-to-medial trajectory. The needle is advanced to position the needle tip at a target location lateral (e.g., a direction away from and perpendicular to a mid-sagittal plan of the subject) to the psoas tendon. For example, the needle tip is positioned lateral to the psoas tendon between the anterior inferior iliac spine (AIIS) and the psoas tendon. In this location, the needle tip can be located medial of the slope of the AIIS and lateral to the psoas tendon.

Precise positioning of the needle tip can be facilitated by advancing the needle along a trajectory aligned with the AIIS. For example, the pharmaceutical composition can be injected while the needle (e.g., a distal portion of the needle proximate the needle tip) is parallel—e.g., substantially parallel, within about 15° of exactly parallel, such as within about 10° of exactly parallel, such as within about 5° of exactly parallel—of the AIIS. Delivery of pharmaceutical compositions at such a location can yield advantageous spread of the pharmaceutical compositions while being distant from the psoas tendon and femoral nerve. For example, delivery in such locations can provide advantageous spread along the pubic brim to the iliacus muscle, and/or along the pubic ramus to the joint capsule. In some embodiments, an in-plane mode of insertion at a relatively acute trajectory can facilitate real-time needle visualization and accurate positioning relative to the psoas tendon, AIIS, and/or other anatomical features of the subject.

Referring to FIG. 1, an example needle trajectory is shown. The needle is advanced using an in-plane mode of insertion along a cephalad-to-caudad and lateral-to-medial trajectory. The injection needle is parallel to the MIS proximate the target location, and the target location is spaced laterally from the psoas tendon, proximate the AIIS.

Alternatively or additionally, administering the composition includes advancing a needle tip of an injection needle to a location between the psoas tendon and the pubic rami. For example, the needle tip is advanced to a target location in the musculofascial plane between the psoas tendon anteriorly and the pubic rami posteriorly. In an example embodiment, advancing the needle tip includes inserting the needle in-plane, relative to an imaging transducer, in a plane between the psoas tendon and the pubic ramus. Such needle advancement and positioning can facilitate delivery of the pharmaceutical composition within the myofascial plane of the psoas muscle and the superior pubic ramus.

In various example embodiments, the injection needle is a standard injection needle, having a size between 18 and 28 gauge, 20 and 24 gauge, or 22 gauge, and a length between 60 mm and 180 mm, 80 mm and 140 mm, or about 120 mm.

In some embodiments, a pharmaceutical composition as disclosed herein is administered in the manner described in Santos et al., J Anesth Clin Res 2019, 10:6, Ahiskalioglu et al., Journal of Clinical Anesthesia 61 (2020) 109650, Short et al., Regional Anesthesia and Pain Medicine—Volume 43, Number 2, February 2018, Tran et al., Reg Anesth Pain Med 2019; 44:257. Peng et al., Reg Anesth Pain Med 2019; 44:415-416, Yu et al., Reg Anesth Pain Med 2019; 44:611-613, Giron Arango L, Peng P. Reg Anesth Pain Med 2019; 44:613-614. each of which is incorporated by reference herein in its entirety.

In some embodiments, treatment of hip pain as disclosed herein is combined with surgical and/or non-surgical treatments. In some embodiments, treatment of hip pain as disclosed herein is used as acute or chronic treatment. In some embodiments, treatment of hip pain as disclosed herein is used as a preoperative, perioperative or operative intervention, for example to treat pain in and around the hip joint, such as pain related to innervation of the hip joint supplied by sensory nerves.

In some embodiments, the methods disclosed herein may be used together with, prior to, or subsequently to one or more of the method disclosed in international applications PCT/US2021/012266, filed Jan. 6, 2021, PCT/US2021/012275, filed Jan. 6, 2021, and PCT/US2021/012269, filed Jan. 6, 2021, each of which is incorporated herein in its entirety, and in U.S. provisional applications 63/066,573, filed Aug. 17, 2020, 62/957,694, filed Jan. 6, 2020, 63/066,477, filed Aug. 17, 2020, 62/959,550, filed Jan. 6, 2020, 63/064,760, filed Aug. 12, 2020, 62/959,640, filed Jan. 10, 2020, each of which is incorporated herein in its entirety.

In some embodiments the at least one polyhydroxy carboxylic acid is selected from the group consisting of glucuronic acid, gluconic acid and tartaric acid.

In some embodiments the amphipathic lipid is selected from the group consisting of phosphatidylcholines, phosphatidylethanolamines, sphingomyelins, lysophosphatidylcholines, lysophosphatidylethanolamines, phosphatidylglycerols, phosphatidylserines, phosphatidylinositols, phosphatidic acids, cardiolipins, diacyl dimethylammonium propanes, and stearylamines.

In some embodiments the neutral lipid comprises at least one triglyceride.

In some embodiments the method comprises administering a therapeutically effective amount of the pharmaceutical composition.

In some embodiments the pharmaceutical composition comprises a therapeutically effective amount of bupivacaine phosphate. In some embodiments wherein the pharmaceutical composition comprises bupivacaine phosphate in an amount equivalent to from about 20 mg to about 300 mg of bupivacaine. In some embodiments the pharmaceutical composition comprises an amount equivalent to from about 133 mg to about 266 mg of bupivacaine.

In some embodiments the pharmaceutical composition comprises an amount equivalent to from about 10 mg to about 300 mg of bupivacaine. In some embodiments the pharmaceutical composition comprises an amount equivalent to from about 133 mg to about 266 mg of bupivacaine. In some embodiments the pharmaceutical composition comprises an amount equivalent to from about 10 mg to about 70 mg of bupivacaine. In some embodiments the pharmaceutical composition comprises an amount equivalent to from about 20 mg to about 60 mg of bupivacaine. In some embodiments the pharmaceutical composition comprises an amount equivalent to from about 20 mg to about 50 mg of bupivacaine. In some embodiments the pharmaceutical composition comprises an amount equivalent to from about 20 mg to about 40 mg of bupivacaine. In some embodiments the pharmaceutical composition comprises an amount equivalent to from about 20 mg to about 30 mg of bupivacaine. In some embodiments the pharmaceutical composition comprises an amount equivalent to from about 30 mg to about 60 mg of bupivacaine. In some embodiments the pharmaceutical composition comprises an amount equivalent to from about 30 mg to about 50 mg of bupivacaine. In some embodiments the pharmaceutical composition comprises an amount equivalent to from about 30 mg to about 40 mg of bupivacaine. In some embodiments the amount of the pharmaceutical composition described herein is equivalent to from about 10 mg to about 70 mg of bupivacaine. In some embodiments the amount of the pharmaceutical composition described herein is equivalent to from about 10 mg to about 60 mg of bupivacaine. In some embodiments the amount of the pharmaceutical composition described herein is equivalent to from about 20 mg to about 60 mg of bupivacaine. In some embodiments the amount of the pharmaceutical composition described herein is equivalent to from about 20 mg to about 50 mg of bupivacaine. In some embodiments the amount of the pharmaceutical composition described herein is equivalent to from about 20 mg to about 40 mg of bupivacaine. In some embodiments the amount of the pharmaceutical composition described herein is equivalent to from about 20 mg to about 30 mg of bupivacaine. In some embodiments the amount of the pharmaceutical composition described herein is equivalent to from about 30 mg to about 60 mg of bupivacaine. In some embodiments the amount of the pharmaceutical composition described herein is equivalent to from about 30 mg to about 50 mg of bupivacaine. In some embodiments the amount of the pharmaceutical composition described herein is equivalent to from about 30 mg to about 40 mg of bupivacaine.

In some embodiments the method comprises administering the pharmaceutical composition by epidural injection.

In some embodiments the method does not comprise administering the pharmaceutical composition by epidural injection.

In some embodiments the method comprises administering the pharmaceutical composition by transversus abdominis plane (TAP) block.

In some embodiments method comprises administering the pharmaceutical composition following completion of the hip treatment.

In some embodiments method comprises administering the pharmaceutical composition prior to the hip treatment.

In some embodiments method comprises administering the pharmaceutical composition during the hip treatment.

In some embodiments the method comprises administering the pharmaceutical composition by transversus abdominis plane (TAP) block under ultrasound guidance.

In some embodiments the method comprises administering an opioid to the subject following completion of the hip treatment.

In some embodiments of the methods herein, the opioid is administered in a total amount less than 200 mg, such as less than 100 mg, such as less than 50 mg, such as less than 25 mg, such as less than 15 mg, in the first about 72 hours following completion of the hip treatment. In some embodiments, the opioid is oxycodone and the method comprises administering oxycodone in a total amount less than 15 mg·in the first about 72 hours following completion of the hip treatment.

In some embodiments, the method comprises administering one or more morphinans to the subject. In some embodiments, the method comprises administering morphine to the subject. In some more particular embodiments, the morphine is administered to the subject for up to 72 hours following completion of the hip treatment.

In some embodiments, the method comprises administering one or more analgesics to the subject, such as one or more NSAIDs to the subject. In some embodiments, the method comprises administering one or more of ketorolac, acetaminophen or ibuprofen to the subject. In some embodiments, the method comprises administering two or more of ketorolac, acetaminophen or ibuprofen to the subject. In some embodiments, the method comprises administering ketorolac, acetaminophen and ibuprofen to the subject. In some more particular embodiments, the analgesic, such as the NSAID, such as the one or more of ketorolac, acetaminophen or ibuprofen, is administered to the subject for up to 72 hours following completion of the hip treatment.

In some embodiments, the subject has an AUC for VAS pain intensity scores over the first 72 hours following completion of the hip treatment of from about 100 to about 200, such as about 125 to 175, such as about 140 to 160, such as about 150, such as about 147.9.

In some embodiments of the methods herein, the subject has a distress from itchiness score as determined by the OBAS scale of less than 4, such as 0, 1, 2 or 3.

In some embodiments of the methods herein, the plasma Cmax of bupivacaine in the subject is about 150 ng/mL to about 250 ng/mL, such as about 175 ng/mL to about 225 ng/mL, such as about 200 ng/mL, such as about 210 mg/mL, for an amount of the pharmaceutical composition described herein that is equivalent to about 133 mg of bupivacaine. In some embodiments, the Cmax occurs after about 48 hours following completion of the hip treatment. In some embodiments, the Cmax occurs after about 72 hours following completion of the hip treatment.

In some embodiments of the methods herein, the plasma Cmax of bupivacaine in the subject is about 300 ng/mL to about 550 ng/mL, such as about 350 ng/mL to about 500 ng/mL, such as about 450 mg/mL, such as about 460 ng/mL, for an amount of the pharmaceutical composition described herein that is equivalent to about 266 mg of bupivacaine. In some embodiments, the Cmax occurs after about 48 hours following completion of the hip treatment. In some embodiments, the Cmax occurs after about 72 hours following completion of the hip treatment.

In some embodiments of the methods herein, the plasma Cmax of bupivacaine in the subject is less than about 850 ng/mL, such as less than about 800 ng/mL, such as less than about 750 ng/mL, such as less than about 700 ng/mL, such as less than about 650 ng/mL, such as less than about 600 ng/mL.

In some embodiments, the subject is a female human.

In some embodiments of the methods herein, the subject is a first subject, wherein in the first about 72 hours following completion of the hip treatment the opioid is administered to the first subject in a total amount that is lower than a total amount of an opioid that is administered to a second subject in the first about 72 hours following completion of a hip treatment in the second subject, wherein a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, is not administered to the second subject.

In some embodiments of the methods herein, the subject is a first subject, wherein in the first about 72 hours following completion of the hip treatment the opioid is administered to the first subject in a total amount that is lower than a total amount of an opioid that is administered to a second subject in the first about 72 hours following completion of a hip treatment in the second subject, wherein a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, is not administered to the second subject.

In some embodiments of the methods herein, the subject is a first subject, wherein in the first about 72 hours following completion of the hip treatment the opioid is administered to the first subject in a total amount that is lower than a total amount of an opioid that is administered to a second subject in the first about 72 hours following completion of a hip treatment in the second subject, wherein a pharmaceutical composition comprising multivesicular liposomes encapsulating bupivacaine phosphate, said multivesicular liposomes comprising:
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and
e) removing the organic solvent from the solvent spherules to form multivesicular liposomes encapsulating bupivacaine phosphate,
is not administered to the second subject.

In some embodiments of the methods herein, the subject is a first subject, wherein in the first about 72 hours following completion of the hip treatment the opioid is administered to the first subject in a total amount that is lower than a total amount of an opioid that is administered to a second subject in the first about 72 hours following completion of a hip treatment in the second subject,
wherein a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi,
is not administered to the second subject.

In some embodiments of the methods herein, the subject is a first subject, wherein in the first about 72 hours following completion of the hip treatment the opioid is administered to the first subject in a total amount that is lower than a total amount of an opioid that is administered to a second subject in the first about 72 hours following completion of a hip treatment in the second subject,
wherein a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 μm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, is not administered to the second subject.

In some embodiments of the methods herein, the subject is a first subject, wherein in the first about 72 hours following completion of the hip treatment the opioid is administered to the first subject in a total amount that is lower than a total amount of an opioid that is administered to a second subject in the first about 72 hours following completion of a hip treatment in the second subject, wherein a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel, wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
is not administered to the second subject.

In some embodiments, the opioid that is administered to the first subject and the opioid that is administered to the second subject are the same. In some embodiments, the opioid that is administered to the first subject and the opioid that is administered to the second subject are different.

In some embodiments of the methods herein, the subject is a first subject, wherein in the first about 72 hours following completion of the hip treatment the opioid is administered to the first subject in a total amount that is lower than a total amount of an opioid that is administered to each of a plurality of second subjects in the first about 72 hours following respective completion of a hip treatment in each of the second subjects, wherein a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, is not administered to the second subjects.

In some embodiments of the methods herein, the subject is a first subject, wherein in the first about 72 hours following completion of the hip treatment the opioid is administered to the first subject in a total amount that is lower than a total amount of an opioid that is administered to each of a plurality of second subjects in the first about 72 hours following respective completion of a hip treatment in each of the second subjects, wherein a pharmaceutical composition comprising: a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome, is not administered to the second subjects.

In some embodiments of the methods herein, the subject is a first subject, wherein in the first about 72 hours following completion of the hip treatment the opioid is administered to the first subject in a total amount that is lower than a total amount of an opioid that is administered to each of a plurality of second subjects in the first about 72 hours following respective completion of a hip treatment in each of the second subjects, wherein a pharmaceutical composition comprising multivesicular liposomes encapsulating bupivacaine phosphate, said multivesicular liposomes comprising:
  bupivacaine or a salt thereof;
  phosphoric acid;
  a lipid component comprising at least one amphipathic lipid and at least one neutral lipid lacking a hydrophilic head group; and,
  optionally, a cholesterol and/or a plant sterol wherein said multivesicular liposomes are made by a process comprising:
  a) preparing a first aqueous component comprising phosphoric acid;
  b) preparing a lipid component comprising at least one organic solvent, at least one amphipathic lipid, and at least one neutral lipid lacking a hydrophilic head group;
  c) mixing said first aqueous component and said lipid component to form a water-in-oil emulsion, wherein at least one component comprises bupivacaine or a salt thereof;
  d) mixing said water-in-oil emulsion with a second aqueous component to form solvent spherules; and
  e) removing the organic solvent from the solvent spherules to form multivesicular liposomes encapsulating bupivacaine phosphate,
  is not administered to the second subjects.

In some embodiments of the methods herein, the subject is a first subject, wherein in the first about 72 hours following completion of the hip treatment the opioid is administered to the first subject in a total amount that is lower than a total amount of an opioid that is administered to each of a plurality of second subjects in the first about 72 hours following respective completion of a hip treatment in each of the second subjects, wherein a multivesicular liposomal particle pharmaceutical composition made by a process comprising: a) providing a volume of first emulsion by mixing a volume of a first aqueous phase and a volume of a volatile water-immiscible solvent phase, said solvent phase comprising at least one amphipathic lipid and at least one neutral lipid; b) mixing and emulsifying said first emulsion and a volume of a second aqueous phase in a high shear mixer to provide a volume of a second emulsion, said second emulsion comprising a continuous aqueous phase; and c) removing the volatile water-immiscible solvent from the second emulsion to form a volume of multivesicular liposomal particle composition, wherein said solvent removal comprises contacting the second emulsion with an inert gas flow; and wherein said process further comprises primary filtration of the multivesicular liposomal particle composition by cross-flow filtration using a filter having a membrane where the multivesicular liposomal particle composition does not pass through the membrane; wherein all steps are carried out under aseptic conditions, and wherein all solutions are sterile filtered, and wherein the multivesicular liposomal particle composition is immediately suitable for administration into humans; and wherein the primary filtration comprises: a first concentration of the multivesicular liposomal particle composition; and a buffer exchange, resulting in a pH of the multivesicular liposomal particle composition of between about 5 and about 8, and the primary filtration is conducted at a transmembrane pressure of from about 0.1 psi to about 20 psi, such as to about 7 psi, is not administered to the second subjects.

In some embodiments of the methods herein, the subject is a first subject, wherein in the first about 72 hours following completion of the hip treatment the opioid is administered to the first subject in a total amount that is lower than a total amount of an opioid that is administered to each of a plurality of second subjects in the first about 72 hours following respective completion of a hip treatment in each of the second subjects,
    wherein a multivesicular liposomal particle pharmaceutical composition of pre-determined, uniform size distribution, made by a process comprising: a) providing a first emulsion by mixing a first aqueous phase and a volatile water-immiscible solvent phase, said solvent phase comprising at least one amphipathic lipid and at least one neutral lipid; b) mixing and emulsifying said first emulsion and a second aqueous phase in a mixer to provide a second emulsion, said second emulsion comprising a continuous aqueous phase; c) sparging the volatile water-immiscible solvent from the second emulsion to form an aqueous suspension of multivesicular liposomal particles by bubbling an inert gas through the second emulsion using at least one sparge ring, at least one sparge tube or at least one fit; d) primary filtration of the aqueous suspension of multivesicular liposomal particles by cross-flow filtration using a filter to exchange the second aqueous phase with an aqueous component to provide an initial volume of aqueous media, wherein the filter has a membrane pore size from 0.07 to 0.45 µm; e) secondary filtration by cross-flow filtration to reduce the initial volume to provide a subsequent volume of aqueous media that is 10% to 90% of the initial volume, further wherein the cross-flow filtration is carried out with a process-scale tangential flow filter with a filtration area of 23 square feet or more, wherein all steps are carried out under aseptic conditions, f) the composition is prepared in quantities or batches greater than a liter; wherein the first emulsion is mixed in a first emulsification vessel of at least 10 liters in volume; and g) wherein the uniform size distribution has a number weighted mean particle size of at least 10 microns, is not administered to the second subjects.

In some embodiments of the methods herein, the subject is a first subject, wherein in the first about 72 hours following completion of the hip treatment the opioid is administered to the first subject in a total amount that is lower than a total amount of an opioid that is administered to each of a plurality of second subjects in the first about 72 hours following respective completion of a hip treatment in each of the second subjects,
    wherein a composition comprising multivesicular liposomes comprising bupivacaine or a salt thereof and having a structure including multiple non-concentric chambers and comprising at least one amphipathic lipid and at least one neutral lipid, wherein said multivesicular liposomes are made by a process comprising removing organic solvent from multivesicular liposomes pre-droplets that comprise a first component core and an aqueous phase shell with an evaporation apparatus, the evaporation apparatus comprising: a solvent removal vessel having a top, a bottom and a circular wall; at least one atomizing nozzle; a carrier gas entrance orifice; a solvent removal gas exit orifice centrally connected to the top; and a product exit orifice connected to the bottom of the vessel,
    wherein the process comprises: introducing the pre-droplets to the solvent removal vessel; applying a carrier gas in a tangential direction to the circular wall through the carrier gas entrance orifice; and removing a solvent removal gas through the solvent removal gas exit orifice to provide the large diameter synthetic membrane vesicles,
is not administered to the second subjects.

In some embodiments, the opioid that is administered to the first subject and the opioid that is administered to at least one of the second subjects are the same. In some embodiments, the opioid that is administered to the first subject and the opioid that is administered to at least one of the second subjects are different. In some embodiments, the opioid that is administered to the first subject and the opioids that are administered to the second subjects are the same. In some embodiments, the opioid that is administered to the first subject and the opioids that are administered to the second subjects are different. In some embodiments, the total amount of an opioid that is administered to each of a plurality of second subjects is a mean total amount.

In some embodiments of the methods herein, non-liposomal bupivacaine or a salt thereof, such as bupivacaine hydrochloride, is administered to the second subject following completion of the hip treatment in the second subject.

In some embodiments of the methods herein, the opioid is administered to the first subject in a total amount that is at least about 20% lower, such as at least about 30% lower, such as at least about 40% lower, such as at least about 50% lower than the total amount of the opioid that is administered to the second subject. In some embodiments of the methods herein, the opioid is administered to the first subject in a total amount that is up to 100% lower (that is, no opioid is administered to the first subject), such as up to 90% lower, such as up to 80% lower, such as up to 70% lower, such as up to 60% lower, than the total amount of the opioid that is administered to the second subject.

In some embodiments of the methods herein, in the first about 72 hours following completion of the hip treatment in the first subject the opioid is administered to the first subject in a total amount that is at least about 20% lower, such as at least about 30% lower, such as at least about 40% lower, such as at least about 50% lower than the total amount of the opioid that is administered to the second subject in the first about 72 hours following completion of the hip treatment in the second subject. In some embodiments of the methods herein, the opioid is administered to the first subject in a total amount that is up to 100% lower (that is, no opioid is administered to the first subject), such as up to 90% lower, such as up to 80% lower, such as up to 70% lower, such as up to 60% lower, than the total amount of the opioid that is administered to the second subject.

In some embodiments of the methods herein, in the first about 24 hours following completion of the hip treatment in the first subject the opioid is administered to the first subject in a total amount that is lower than the total amount of an opioid that is administered to the second subject in the first about 24 hours following completion of the hip treatment in the second subject. In some embodiments of the methods herein, in the first about 24 hours following completion of the hip treatment in the first subject the opioid is administered to the first subject in a total amount that is at least about 20% lower, such as at least about 30% lower, such as at least about 40% lower, such as at least about 50% lower than the total amount of the opioid that is administered to the second subject in the first about 24 hours following completion of the hip treatment in the second subject. In some embodiments of the methods herein, the opioid is administered to the first subject in a total amount that is up to 100% lower (that is, no opioid is administered to the first subject), such as up to 90% lower, such as up to 80% lower, such as up to 70% lower, such as up to 60% lower, than the total amount of the opioid that is administered to the second subject.

In some embodiments of the methods herein, in the first about 48 hours following completion of the hip treatment in the first subject the opioid is administered to the first subject in a total amount that is lower than the total amount of an opioid that is administered to the second subject in the first about 48 hours following completion of the hip treatment in the second subject. In some embodiments of the methods herein, in the first about 48 hours following completion of the hip treatment in the first subject the opioid is administered to the first subject in a total amount that is at least about 20% lower, such as at least about 30% lower, such as at least about 40% lower, such as at least about 50% lower than the total amount of the opioid that is administered to the second subject in the first about 48 hours following completion of the hip treatment in the second subject. In some embodiments of the methods herein, the opioid is administered to the first subject in a total amount that is up to 100% lower (that is, no opioid is administered to the first subject), such as up to 90% lower, such as up to 80% lower, such as up to 70% lower, such as up to 60% lower, than the total amount of the opioid that is administered to the second subject.

In some embodiments of the methods herein, in the first about 7 days following completion of the hip treatment in the first subject the opioid is administered to the first subject in a total amount that is lower than the total amount of an opioid that is administered to the second subject in the first about 7 days following completion of the hip treatment in the second subject. In some embodiments of the methods herein, in the first about 7 days following completion of the hip treatment in the first subject the opioid is administered to the first subject in a total amount that is at least about 20% lower, such as at least about 30% lower, such as at least about 40% lower, such as at least about 50% lower than the total amount of the opioid that is administered to the second subject in the first about 7 days following completion of the hip treatment in the second subject. In some embodiments of the methods herein, the opioid is administered to the first subject in a total amount that is up to 100% lower (that is, no opioid is administered to the first subject), such as up to 90% lower, such as up to 80% lower, such as up to 70% lower, such as up to 60% lower, than the total amount of the opioid that is administered to the second subject.

In some embodiments of the methods herein, in the first about 14 days following completion of the hip treatment in the first subject the opioid is administered to the first subject in a total amount that is lower than the total amount of an opioid that is administered to the second subject in the first about 14 days following completion of the hip treatment in the second subject. In some embodiments of the methods herein, in the first about 14 days following completion of the hip treatment in the first subject the opioid is administered to the first subject in a total amount that is at least about 20% lower, such as at least about 30% lower, such as at least about 40% lower, such as at least about 50% lower than the total amount of the opioid that is administered to the second subject in the first about 14 days following completion of the hip treatment in the second subject. In some embodiments of the methods herein, the opioid is administered to the first subject in a total amount that is up to 100% lower (that is, no opioid is administered to the first subject), such as up to 90% lower, such as up to 80% lower, such as up to 70% lower, such as up to 60% lower, than the total amount of the opioid that is administered to the second subject.

In some embodiments, the opioid that is administered to the first subject and the opioid that is administered to the second subject are the same. In some embodiments, the opioid that is administered to the first subject and the opioid that is administered to the second subject are different.

In some embodiments of the methods herein, the first subject has an AUC for VAS pain intensity scores over the first 72 hours following completion of the hip treatment in the first subject of from about 100 to about 200, such as about 125 to 175, such as about 140 to 160, such as about 150, such as about 147.9; and the second subject has an AUC for VAS pain intensity scores over the first 72 hours following completion of the hip treatment in the second subject of from about 150 to about 250, such as about 165 to 200, such as about 170 to 190, such as about 175 to 180, such as about 178.5.

In some embodiments of the methods herein, the first subject has an AUC for VAS pain intensity scores over the first 72 hours following completion of the hip treatment in the first subject that is at least about 10% lower, such as at least about 17% lower, such as about 27% to about 25% lower, such as at least about 25% lower, than the AUC for VAS pain intensity scores for the second subject over the first 72 hours following completion of the hip treatment in the second subject. In some embodiments the first subject has an AUC for VAS pain intensity scores over the first 72 hours following completion of the hip treatment in the first subject that is up to 100% lower (that is, the AUC is 0), such as up to 90% lower, such as up to 80% lower, such as up to 70% lower, such as up to 60% lower, than the AUC for VAS pain intensity scores for the second subject.

In some embodiments of the methods herein, the first subject has a distress from itchiness score as determined by the OBAS scale that is lower than for the second subject.

In some embodiments of the methods herein, the plasma concentration of bupivacaine in the first subject after about 120 hours following completion of the hip treatment in the first subject is at least about 10%, such as least about 20% higher, such as at least about 30% higher, such as at least about 40% higher, such as 50% higher than the plasma concentration of bupivacaine in the second subject after about 120 hours following completion of the hip treatment in the second subject. In some embodiments, the plasma concentration is up to 500% higher, such as up to 400% higher, such as up to 300% higher, such as up to 200% higher, such as up to 100% higher, than the plasma concentration in the second subject.

In some embodiments, the method does not comprise administering an opioid to the subject following completion of the cesarean section.

In some embodiments, the method does not comprise administering one or more morphinans to the subject. In some embodiments, the method does not comprise administering morphine to the subject.

In some embodiments, the method does not comprise administering an opioid to the first subject following completion of the cesarean section.

In some embodiments, the method does not comprise administering one or more morphinans to the first subject. In some embodiments, the method does not comprise administering morphine to the first subject.

In some embodiments, the method comprises administering into the subject an amount of the pharmaceutical composition described herein that is equivalent to about 20 to about 300 mg of bupivacaine. In some embodiments, the method comprises administering into the subject an amount of the pharmaceutical composition described herein that is equivalent to about 100 to about 300 mg of bupivacaine. In some embodiments, the method comprises administering into the subject an amount of the pharmaceutical composition described herein that is equivalent to about 133 to about 300 mg of bupivacaine. In some embodiments, the method comprises administering into the subject an amount of the pharmaceutical composition described herein that is equivalent to about 133 to about 266 mg of bupivacaine. In some embodiments, the method comprises administering into the subject about 20 mL of the pharmaceutical composition described herein containing about 266 mg of bupivacaine.

In some embodiments, the method comprises administering into the first subject an amount of the pharmaceutical composition described herein that is equivalent to about 20 to about 300 mg of bupivacaine. In some embodiments, the method comprises administering into the first subject an amount of the pharmaceutical composition described herein that is equivalent to about 100 to about 300 mg of bupivacaine. In some embodiments, the method comprises administering into the first subject an amount of the pharmaceutical composition described herein that is equivalent to about 133 to about 300 mg of bupivacaine. In some embodiments, the method comprises administering into the first subject an amount of the pharmaceutical composition described herein that is equivalent to about 133 to about 266 mg of bupivacaine. In some embodiments, the method comprises administering into the first subject about 20 mL of the pharmaceutical composition described herein containing about 266 mg of bupivacaine.

In some embodiments, the method comprises administering into the subject the pharmaceutical composition comprising bupivacaine phosphate in an amount equivalent to 266 mg of bupivacaine and non-liposomal bupivacaine in an amount equivalent to 44 mg of bupivacaine base.

In some embodiments, the method comprises administering into the first subject the pharmaceutical composition comprising bupivacaine phosphate in an amount equivalent to 266 mg of bupivacaine and non-liposomal bupivacaine in an amount equivalent to 44 mg of bupivacaine, and administering into the second subject non-liposomal bupivacaine in an amount equivalent to 44 mg of bupivacaine.

In some embodiments the non-liposomal bupivacaine may be, for example, in the form of the hydrochloride salt of bupivacaine.

In some embodiments, the method comprises administering one or more non-opioid analgesics to the subject. In some embodiments, the one or more non-opioid analgesics are one or more NSAIDs. In some embodiments, the one or more non-opioid analgesics are one or more of ketorolac, acetaminophen or ibuprofen. Thus, in some embodiments, the method comprises administering one or more of ketorolac, acetaminophen or ibuprofen to the subject, wherein the one or more of ketorolac, acetaminophen or ibuprofen, is administered to the subject for up to 72 hours following completion of the hip treatment in the following amounts:
  IV ketorolac 15 mg once at the time of skin incision closure and prior to the TAP infiltration
  Intravenous (IV) acetaminophen 1000 mcg at the time of skin incision closure
  Scheduled oral (PO) acetaminophen 650 mg at the end of surgery and every 6 hours (q6h) for up to 72 hours
  Scheduled PO ibuprofen 600 mg at the end of surgery and q6h for up to 72 hours In some embodiments, the method comprises administering an opioid to a subject, wherein one or more opioids are administered in the following amounts:
  oral immediate-release oxycodone at 5-10 mg every 4 hours or as needed
  IV morphine at 1-2 mg or hydromorphone initiated at 0.3-0.5 mg every 4 hours or as needed In some embodiments, the first subject is a female human and the second subject is a female human.

In some embodiments of any of the methods disclosed herein, the method produces postsurgical local analgesia.

In some embodiments of any of the methods disclosed herein, the method produces postsurgical regional analgesia.

Unless otherwise defined, all technical and scientific terms used herein have the same meaning as commonly understood by one of ordinary skill in the art to which this invention belongs. Although methods and materials similar to those described herein can be used in the practice or testing of the present invention, suitable methods and materials are described below.

All publications, patent applications, patents, and other references mentioned herein are incorporated by reference in their entirety. In addition, the materials, methods, and examples are illustrative only and not intended to be limiting.

The term "therapeutically effective" as it pertains to bupivacaine or a salt thereof, such as bupivacaine phosphate, present in the pharmaceutical compositions described herein, means that an anesthetic present in the first aqueous phase within the multivesicular liposome is released in a manner sufficient to achieve a particular level of anesthesia. Exact dosages will vary depending on such factors as the particular anesthetic, as well as patient factors such as age, sex, general condition, and the like. Those of skill in the art can readily take these factors into account and use them to establish effective therapeutic concentrations without resort to undue experimentation.

As used herein, "non-liposomal bupivacaine" refers to bupivacaine or a salt thereof that is not in liposomal form. For example, "non-liposomal bupivacaine" refers to bupivacaine or a salt thereof that is not comprised in a multivesicular liposome. The term "non-liposomal bupivacaine" encompasses compositions comprising bupivacaine, or a salt thereof, that is not in liposomal form. As used herein, "completion" of the cesarean section surgery occurs when skin incision closure is complete.

As used herein, a "VAS pain intensity score" refers to the Visual Analog Scale pain intensity score described in Delgado et al., *J Am Acad Orthop Surg Glob Res Rev.* 2018 March; 2(3):e 088, published online 2018 Mar. 23. doi: 10.5435/JAAOSGlobal-D-17-00088, incorporated by reference herein in its entirety.

The compositions used in the methods disclosed herein comprise a) a multivesicular liposome comprising: at least one amphipathic lipid, and at least one neutral lipid; and b) an aqueous phase comprising: at least one polyhydroxy carboxylic acid and at least one di- or tri-protic mineral acid; and bupivacaine phosphate, wherein the aqueous phase is encapsulated within the multivesicular liposome.

In some embodiments the aqueous phase further comprises hydrochloric acid.

Multivesicular liposomes (or "MVL", which is used herein to refer to a multivesicular liposome or a plurality of multivesicular liposomes) are lipid vesicles having multiple non-concentric internal aqueous chambers having internal membranes distributed as a network throughout the MVL. The chambers may contain acids which are effective to enable the encapsulation of bupivacaine or a salt thereof and to modulate its release rate. A preparation of MVL is described, for example, in Kim et al., Biochim. Biophys. Acta 728, 339-348, 1983. In some embodiments, a MVL is prepared in accordance with a process as described in U.S. Pat. No. 9,192,575, incorporated by reference herein in its entirety. In some embodiments, a MVL is prepared in accordance with a process as described in U.S. Pat. No. 8,182,835, incorporated by reference herein in its entirety. In some embodiments, a MVL is prepared in accordance with a process as described in U.S. Pat. No. 8,834,921, incorporated by reference herein in its entirety. In some embodiments, a MVL is prepared in accordance with a process as described in U.S. Pat. No. 9,205,052, incorporated by reference herein in its entirety.

In some embodiments the multivesicular liposomes ("MVL") are made by the following process. A "water-in-oil" type emulsion containing a non-hydrohalic acid salt of bupivacaine, such as bupivacaine phosphate, is formed from two immiscible phases, a lipid phase and a first aqueous phase. The lipid phase is made up of at least one amphipathic lipid and at least one neutral lipid in a volatile organic solvent. The term "amphipathic lipid" refers to molecules having a hydrophilic "head" group and a hydrophobic "tail" group and may have membrane-forming capability. As used herein, amphipathic lipids include those having a net negative charge, a net positive charge, and zwitterionic lipids (having no net charge at their isoelectric point). The term "neutral lipid" refers to oils or fats that have no vesicle-forming capability by themselves, and lack a charged or hydrophilic "head" group. Examples of neutral lipids include, but are not limited to, glycerol esters, glycol esters, tocopherol esters, sterol esters which lack a charged or hydrophilic "head" group, and alkanes and squalenes.

The amphipathic lipid is chosen from a wide range of lipids having a hydrophobic region and a hydrophilic region in the same molecule. Suitable amphipathic lipids are zwitterionic phospholipids, including phosphatidylcholines, phosphatidylethanolamines, sphingomyelins, lysophosphatidylcholines, and lysophosphatidylethanolamines. Also suitable are the anionic amphipathic phospholipids such as phosphatidylglycerols, phosphatidylserines, phosphatidylinositols, phosphatidic acids, and cardiolipins. Also suitable are the cationic amphipathic lipids such as acyl trimethylammonium propanes, diacyl dimethylammonium propanes, and stearylamines.

Suitable neutral lipids are triglycerides, propylene glycol esters, ethylene glycol esters, and squalene. Examples of triglycerides useful in the present invention are triolein, tripalmitolein, trimyristolein, trilinolein, tributyrin, tricaproin, tricaprylin, and tricaprin. The fatty chains in the triglycerides useful in the present invention can be all the same, or not all the same (mixed chain triglycerides), including all different. Both saturated and unsaturated fatty chains are useful in the present invention. The propylene glycol esters can be mixed diesters of caprylic and capric acids.

Many types of volatile organic solvents can be used in the present invention, including ethers, esters, halogenated ethers, hydrocarbons, halohydrocarbons, or Freons. For example, diethyl ether, chloroform, tetrahydrofuran, ethyl acetate, Forane, and any combinations thereof are suitable for use in making the compositions of the present invention.

Optionally, other components are included in the lipid phase. Among these are cholesterol or plant sterols.

The first aqueous phase includes bupivacaine or a salt thereof, such as bupivacaine phosphate, at least one polyhydroxy carboxylic acid, and at least one di- or tri-protic mineral acid. In some embodiments, also included is hydrochloric acid. The di- or tri-protic mineral acids include sulfuric acid, and phosphoric acid. Also included in the first aqueous phase are such polyhydroxy carboxylic acids as glucuronic acid, gluconic acid, and tartaric acid. The di- and tri-protic mineral acids and the polyhydroxy organic acids are present in the first aqueous phase in concentrations of from 0.01 mM to about 0.5 M, or preferably from about 5 mM to about 300 mM. When hydrochloric acid is used, it is present in lower amounts, from about 0.1 mM to about 50 mM, or preferably from about 0.5 mM to about 25 mM.

The lipid phase and first aqueous phase are mixed by mechanical turbulence, such as through use of rotating or vibrating blades, shaking, extrusion through baffled structures or porous pipes, by ultrasound, or by nozzle atomization, to produce a water-in-oil emulsion. Thus, bupivacaine or a salt thereof, such as bupivacaine phosphate, is encapsulated directly in the first step of MVL manufacture.

The whole water-in-oil emulsion is then dispersed into a second aqueous phase by means described above, to form solvent spherules suspended in the second aqueous phase. The term "solvent spherules" refers to a microscopic spheroid droplet of organic solvent, within which are suspended multiple smaller droplets of aqueous solution. The resulting solvent spherules therefore contain multiple aqueous droplets with the bupivacaine or a salt thereof, such as bupivacaine phosphate, dissolved therein. The second aqueous phase can contain additional components such as glucose, and/or lysine.

The volatile organic solvent is then removed from the spherules, for instance by surface evaporation from the suspension: When the solvent is substantially or completely evaporated, MVL are formed. Gases which can be used for the evaporation include nitrogen, argon, helium, oxygen, hydrogen, and carbon dioxide. Alternatively, the volatile solvent can be removed by sparging, rotary evaporation, or with the use of solvent selective membranes.

In some embodiments, an MVL is prepared in accordance with a process as described in U.S. Pat. No. 10,398,648, incorporated by reference herein in its entirety. In some embodiments, a MVL is prepared in accordance with a process as described in U.S. Pat. No. 9,585,838 incorporated by reference herein in its entirety.

In some embodiments, a MVL is prepared in accordance with a process as described in US 2011-0250264, US 2013-0306759, US 2013-0177634, US 2013-0177633, US 2013-0177635, US 2013-0195965, US 2013-0177636, US 2013-0183373, US 2013-0177638, US 2013-0177637, US 2013-0183372, US 2013-0183375, US 2016-0361260 or US 2018-0092847, each of which is incorporated by reference herein in its entirety.

EXAMPLES

Example 1

A pharmaceutical composition as described herein is injected into the hip of the subject, directing the needle tip laterally to the psoas tendon, as shown in FIG. 1.

It will be understood that various modifications may be made without departing from the spirit and scope of the invention. Accordingly, other embodiments are within the scope of the following claims.

The invention claimed is:

1. A method of reducing an amount of a non-opioid analgesic administered to a subject following hip treatment, the method comprising administering to the subject a pharmaceutical composition comprising: a) a multivesicular liposome comprising: at least one amphipathic lipid, and at least one neutral lipid; and b) an aqueous phase comprising bupivacaine phosphate, wherein the aqueous phase is encapsulated within the multivesicular liposome, wherein the pharmaceutical composition is administered by a needle injection, wherein a needle tip is located at a distal end of the injection needle and wherein the needle tip is advanced in a cephalad-to-caudad and lateral-to-medial direction away from a musculofascial plane between the psoas tendon and the pubic ramus, and wherein administering the composition occurs while the needle tip is located lateral to the psoas tendon such that the needle tip is positioned between the anterior inferior iliac spine and psoas tendon.

2. A method of reducing an amount of a non-opioid analgesic administered to a subject following hip treatment, the method comprising administering to the subject a pharmaceutical composition comprising multivesicular liposomes encapsulating bupivacaine phosphate, said multivesicular liposomes comprising:
bupivacaine or a salt thereof;
phosphoric acid;
a lipid component comprising at least one amphipathic lipid and at least one neutral lipid lacking a hydrophilic head group; and,
optionally, a cholesterol and/or a plant sterol wherein said multivesicular liposomes are made by a process comprising:
a) preparing a first aqueous component comprising phosphoric acid;
b) preparing a lipid component comprising at least one organic solvent, at least one amphipathic lipid, and at least one neutral lipid lacking a hydrophilic head group;
c) mixing said first aqueous component and said lipid component to form a water-in-oil emulsion, wherein at least one component comprises bupivacaine or a salt thereof;
d) mixing said water-in-oil emulsion with a second aqueous component to form solvent spherules; and e) removing the organic solvent from the solvent spherules to form multivesicular liposomes encapsulating bupivacaine phosphate,
wherein the pharmaceutical composition is administered by a needle injection, wherein a needle tip is located at a distal end of the injection needle and wherein the needle tip is advanced in a cephalad-to-caudad and lateral-to-medial direction away from a musculofascial plane between the psoas tendon and the pubic ramus, and wherein administering the composition occurs while the needle tip is located lateral to the psoas tendon such that the needle tip is positioned between the anterior inferior iliac spine and psoas tendon.

3. The method of claim 1, wherein the aqueous phase further comprises hydrochloric acid.

4. The method of claim 1, wherein the amphipathic lipid is selected from the group consisting of phosphatidylcholines, phosphatidylethanolamines, sphingomyelins, lysophosphatidylcholines, lysophosphatidylethanolamines, phosphatidylglycerols, phosphatidylserines, phosphatidylinositols, phosphatidic acids, cardiolipins, diacyl dimethylammonium propanes, and stearylamines.

5. The method of claim 1, wherein the neutral lipid is at least one triglyceride.

6. The method of claim 1, wherein the pharmaceutical composition comprises a therapeutically effective amount of bupivacaine phosphate.

7. The method of claim 1, wherein the pharmaceutical composition comprises bupivacaine phosphate in an amount equivalent to from about 20 mg to about 300 mg of bupivacaine.

8. The method of claim 7, wherein the pharmaceutical composition comprises bupivacaine phosphate in an amount equivalent to from about 133 mg to about 266 mg of bupivacaine.

9. The method of claim 1, wherein the method does not comprise administering the pharmaceutical composition by epidural injection.

10. The method of claim 1, wherein the method does not comprise administering an opioid to the subject following completion of the treatment.

11. The method of claim 1, wherein the method comprises administering an opioid to the subject following completion of the treatment.

12. The method of claim 11, wherein the method comprises administering to the subject following completion of the treatment an amount of an opioid selected from the group consisting of: less than 200 mg, less than 100 mg, less than 50 mg, and less than 25 mg.

13. The method of claim 12, wherein the opioid is oxycodone and the method comprises administering oxycodone in a total amount less than or equal to 10 mg or administering morphine in a total amount less than or equal to 15 mg in the first about 72 hours following completion of the treatment.

14. The method of claim 1, wherein the subject has an AUC for VAS pain intensity scores over the first 72 hours following completion of the treatment of from about 100 to about 200.

15. The method of claim 1, wherein the subject has a distress from itchiness score as determined by the OBAS scale of less than 4.

16. The method of claim 1, wherein the plasma concentration of bupivacaine in the subject after about 120 hours following completion of the treatment is about 150 ng/mL to about 250 ng/mL, for an amount of the pharmaceutical composition described herein that is equivalent to about 133 mg of bupivacaine.

17. The method of claim 1, wherein the method does not comprise administering an opioid to the subject following completion of the hip treatment.

18. A method of reducing hip pain in a subject, the method comprising administering to the subject a pharmaceutical composition comprising multivesicular liposomes encapsulating bupivacaine phosphate, said multivesicular liposomes comprising:
   bupivacaine or a salt thereof;
   phosphoric acid;
   a lipid component comprising at least one amphipathic lipid and at least one neutral lipid lacking a hydrophilic head group; and,
   optionally, a cholesterol and/or a plant sterol wherein said multivesicular liposomes are made by a process comprising:
   a) preparing a first aqueous component comprising phosphoric acid;
   b) preparing a lipid component comprising at least one organic solvent, at least one amphipathic lipid, and at least one neutral lipid lacking a hydrophilic head group;
   c) mixing said first aqueous component and said lipid component to form a water-in-oil emulsion, wherein at least one component comprises bupivacaine or a salt thereof;
   d) mixing said water-in-oil emulsion with a second aqueous component to form solvent spherules; and
   e) removing the organic solvent from the solvent spherules to form multivesicular liposomes encapsulating bupivacaine phosphate, wherein the pharmaceutical composition is administered by needle injection, wherein the needle tip is located at a distal end of an injection needle and the needle is advanced using an in-plane mode of insertion relative to an imaging transducer, and wherein administering the composition occurs while the needle tip is located lateral to the psoas tendon such that the needle tip is positioned between the anterior inferior iliac spine and psoas tendon.

19. The method of claim 1, wherein the needle has a needle length between 60 mm and 150 mm.

20. The method of claim 1, wherein the needle has a diameter between 25 gauge and 20 gauge.

21. The method of claim 1, wherein administration comprises advancing the needle using an in-plane mode of insertion relative to an imaging transducer.

22. The method of claim 1, wherein injecting the composition occurs while the needle is parallel with the anterior inferior iliac spine (AIIS) proximate the needle tip.

23. The method of claim 16, wherein the plasma concentration of bupivacaine is selected from the group consisting of about 175 ng/mL to about 225 ng/mL, such as about 200 ng/mL, such as about 210 mg/mL.

24. The method of claim 18, wherein the injecting the composition occurs while the needle is parallel with the AIIS proximate the needle tip.

25. The method of claim 24, wherein the distal portion of the needle is within 15 degrees of exactly parallel of the anterior inferior iliac spine.

26. The method of claim 25, wherein the distal portion of the needle is exactly parallel of the anterior inferior iliac spine.

* * * * *